US 8,668,642 B2

(12) United States Patent
Kleyman (10) Patent No.: US 8,668,642 B2
(45) Date of Patent: Mar. 11, 2014

(54) PORT DEVICE INCLUDING RETRACTABLE ENDOSCOPE CLEANER

(75) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 3 days.

(21) Appl. No.: 13/223,332

(22) Filed: Sep. 1, 2011

(65) Prior Publication Data

US 2012/0130189 A1 May 24, 2012

Related U.S. Application Data (60) Provisional application No. 61/416,497, filed on Nov. 23, 2010.

(51) Int. Cl.
*A61B 1/32* (2006.01)
(52) U.S. Cl.
USPC .......................................................... 600/204
(58) Field of Classification Search
USPC ................................ 600/201–210, 215, 217;
604/164.01–164.11, 167.01–167.06,
604/266–267, 513, 539, 264; 15/104.03,
15/104.16, 104.2, 246, 250.001
See application file for complete search history.

(56) References Cited

U.S. PATENT DOCUMENTS

| 16,680 | A | 2/1857 | Bussell |
| 363,951 | A | 5/1887 | Forster |
| 387,410 | A | 8/1888 | Gillette |
| 449,080 | A | 3/1891 | Mackay |
| 685,088 | A | 10/1901 | Barlow |
| 1,131,349 | A | 3/1915 | Ellis |
| 1,256,831 | A * | 2/1918 | Rogers ............................... 604/1 |
| 2,932,837 | A | 4/1960 | Ver Nooy |
| 3,675,263 | A | 7/1972 | Durham |
| 3,939,519 | A | 2/1976 | Muirhead |
| 4,021,265 | A | 5/1977 | Guenther |
| 4,031,590 | A | 6/1977 | Clavin |
| 4,700,423 | A | 10/1987 | Zuliani |
| 4,715,747 | A | 12/1987 | Behrens |
| 4,798,246 | A | 1/1989 | Best |
| 4,813,097 | A | 3/1989 | Simpson |
| 4,842,578 | A | 6/1989 | Johnson et al. |
| 4,873,778 | A | 10/1989 | Stipp |
| 4,889,106 | A | 12/1989 | Watanabe |

(Continued)

FOREIGN PATENT DOCUMENTS

| EP | 2 289 438 A1 | 3/2011 |
| WO | WO 2007/034202 A1 | 3/2007 |

OTHER PUBLICATIONS

European Search Report for EP 11250794.2-2310 date of completion is Feb. 9, 2012 (6 pages).

(Continued)

*Primary Examiner* — Todd Manahan
*Assistant Examiner* — Eric S Gibson (57) ABSTRACT

A surgical apparatus includes a housing member having leading and trailing ends that define a longitudinal axis. One or more ports longitudinally extend between the leading and trailing ends, and are configured and adapted to receive a surgical instrument therein in a substantially sealed relation. At least one cleaning port longitudinally extends between the leading and trailing ends, and is configured and adapted to receive a cleaning device therein. The cleaning device is configured and adapted to clean surgical instruments positioned within the one or more ports without necessitating removal of the surgical instruments from the one or more ports.

16 Claims, 4 Drawing Sheets

(56) References Cited

U.S. PATENT DOCUMENTS

| | | | |
|---|---|---|---|
| 4,962,607 A | 10/1990 | Baldwin | |
| 5,074,840 A | 12/1991 | Yoon | |
| 5,188,630 A | 2/1993 | Christoudias | |
| 5,295,952 A * | 3/1994 | Pietrafitta | 604/1 |
| 5,337,730 A | 8/1994 | Maguire | |
| 5,366,478 A * | 11/1994 | Brinkerhoff et al. | 606/213 |
| 5,392,766 A | 2/1995 | Masterson et al. | |
| 5,399,161 A | 3/1995 | Williams et al. | |
| 5,419,310 A | 5/1995 | Frassica et al. | |
| 5,437,073 A | 8/1995 | Smith | |
| 5,439,457 A * | 8/1995 | Yoon | 604/358 |
| 5,458,633 A | 10/1995 | Bailey | |
| 5,514,084 A | 5/1996 | Fisher | |
| 5,522,795 A | 6/1996 | Green et al. | |
| 5,555,588 A | 9/1996 | Viesehon | |
| 5,615,439 A | 4/1997 | Bourrelly | |
| 5,709,691 A | 1/1998 | Morejon | |
| 5,814,160 A | 9/1998 | Orlando | |
| 5,913,867 A | 6/1999 | Dion | |
| 5,938,587 A | 8/1999 | Taylor et al. | |
| 5,964,004 A | 10/1999 | Bean | |
| 5,989,183 A | 11/1999 | Reisdorf et al. | |
| 6,017,333 A | 1/2000 | Bailey | |
| 6,045,623 A | 4/2000 | Cannon | |
| 6,126,592 A | 10/2000 | Proch et al. | |
| 6,176,825 B1 | 1/2001 | Chin et al. | |
| 6,183,450 B1 | 2/2001 | Lois | |
| 6,276,017 B1 | 8/2001 | Lino et al. | |
| 6,406,425 B1 | 6/2002 | Chin et al. | |
| 6,464,632 B1 | 10/2002 | Taylor | |
| 6,679,262 B1 | 1/2004 | Morejon | |
| 6,699,331 B1 | 3/2004 | Kritzler | |
| 6,725,492 B2 | 4/2004 | Moore et al. | |
| 6,792,641 B1 | 9/2004 | Laker | |
| 6,800,083 B2 | 10/2004 | Hiblar et al. | |
| 6,875,183 B2 | 4/2005 | Cervi | |
| 6,889,400 B2 | 5/2005 | Kawazoe et al. | |
| 6,920,662 B2 | 7/2005 | Moore | |
| 6,929,601 B2 | 8/2005 | Nakao | |
| 7,051,737 B2 | 5/2006 | Kolobow et al. | |
| 7,060,135 B2 | 6/2006 | Morejon | |
| 7,077,845 B2 | 7/2006 | Hacker et al. | |
| 7,143,829 B2 | 12/2006 | Booth | |
| 7,476,226 B2 | 1/2009 | Weikel et al. | |
| 7,669,600 B2 | 3/2010 | Morejon | |
| 2003/0055404 A1 | 3/2003 | Moutafis | |
| 2003/0139649 A1 | 7/2003 | Kasahara et al. | |
| 2004/0087956 A1 | 5/2004 | Weikel et al. | |
| 2004/0181194 A1 | 9/2004 | Perkins | |
| 2004/0210110 A1 | 10/2004 | Nakao | |
| 2005/0043683 A1 | 2/2005 | Ravo | |
| 2005/0075538 A1 | 4/2005 | Banik et al. | |
| 2005/0131279 A1 | 6/2005 | Boulais et al. | |
| 2005/0154262 A1 | 7/2005 | Banik et al. | |
| 2006/0047186 A1 | 3/2006 | Annecke | |
| 2006/0116551 A1 | 6/2006 | Lovett et al. | |
| 2006/0178556 A1 | 8/2006 | Hasser et al. | |
| 2007/0100276 A1 | 5/2007 | Fanton et al. | |
| 2007/0167682 A1 | 7/2007 | Goldfarb et al. | |
| 2007/0282253 A1 | 12/2007 | Sasaki | |
| 2008/0086106 A1 | 4/2008 | Karami | |
| 2008/0132880 A1 | 6/2008 | Buchman | |
| 2008/0172033 A1 | 7/2008 | Keith et al. | |
| 2008/0188715 A1 | 8/2008 | Fujimoto | |
| 2008/0200765 A1 | 8/2008 | Mondschein | |
| 2008/0319266 A1 | 12/2008 | Poll et al. | |
| 2009/0036745 A1 * | 2/2009 | Bonadio et al. | 600/208 |
| 2009/0044353 A1 | 2/2009 | Galantai et al. | |
| 2009/0064999 A1 | 3/2009 | Marten et al. | |
| 2009/0093752 A1 * | 4/2009 | Richard et al. | 604/24 |
| 2009/0105543 A1 | 4/2009 | Miller et al. | |
| 2009/0118586 A1 | 5/2009 | Griffin | |
| 2009/0131747 A1 | 5/2009 | Chin et al. | |
| 2009/0171154 A1 | 7/2009 | Sutoh | |
| 2009/0209823 A1 | 8/2009 | Yamane | |
| 2009/0264703 A1 | 10/2009 | Pribanic | |
| 2009/0272388 A1 | 11/2009 | Uemura et al. | |
| 2009/0275972 A1 | 11/2009 | Uemura et al. | |
| 2009/0299135 A1 | 12/2009 | Spivey | |
| 2010/0010310 A1 | 1/2010 | Weisenburgh, II et al. | |
| 2010/0048999 A1 | 2/2010 | Boulais et al. | |
| 2010/0076266 A1 | 3/2010 | Boulais et al. | |
| 2010/0240960 A1 * | 9/2010 | Richard | 600/208 |
| 2010/0249526 A1 * | 9/2010 | Shelton et al. | 600/208 |
| 2010/0286484 A1 * | 11/2010 | Stellon et al. | 600/208 |
| 2010/0312060 A1 * | 12/2010 | Widenhouse et al. | 600/201 |

OTHER PUBLICATIONS

European Search Report dated Sep. 27, 2013 from corresponding EP Application No. 11250794.2 (11 pgs.).

* cited by examiner

PORT DEVICE INCLUDING RETRACTABLE ENDOSCOPE CLEANER

CROSS REFERENCE TO RELATED APPLICATION

The present application claims the benefit of and priority to U.S. Provisional Application Ser. No. 61/416,497 filed on Nov. 23, 2010, the entire contents of which are incorporated herein by reference.

BACKGROUND

1. Technical Field

The present disclosure relates generally to a surgical portal apparatus for use in a minimally invasive surgical procedure. More particularly, the surgical portal apparatus includes a cleaning device to facilitate in situ cleaning of surgical instruments placed within the surgical portal apparatus.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. A typical surgical object, such as a laparoscope includes: a housing, an elongated viewing portion shaft extends from one end of the housing, and a viewing portion that is provided in the distal end of the viewing portion shaft. A camera viewfinder extends from the other end of the housing. A camera is connected to the housing and transmits images sighted through the viewing portion to a television monitor on which the images are displayed. During a surgical procedure, the distal end portion of the viewing portion shaft is extended into an incision in the patient's abdominal wall, while the proximal end portion of the viewing portion shaft, the housing and the camera viewfinder remain outside the patient.

During insertion of an endoscope or a laparoscope into the body and during the surgical procedure, debris, e.g., organic matter and moisture may be deposited on the viewing portion of the endoscope. The buildup of debris and/or moisture on the viewing portion impairs visualization of the surgical site, and often necessitates cleaning of the viewing portion. Cleaning of the instruments often necessitates removal of the instruments from the surgical site, thereby increasing the time required to perform the surgical procedure.

SUMMARY

Disclosed herein is a surgical portal apparatus that facilitates in situ cleaning of surgical instruments introduced within a surgical site through the surgical portal apparatus. The surgical portal apparatus includes a cleaning device and a housing member. The housing member includes a leading portion, a trailing portion, and an intermediate portion. The intermediate portion is disposed between the leading and the trailing portions. One or more ports extend longitudinally between the leading and the trailing portions. The one or more ports are configured and adapted to receive a surgical instrument. At least one cleaning port extends between the leading and trailing portions. The at least one cleaning port is configured and adapted to receive, e.g., hold or store, a cleaning device. The cleaning device is configured and adapted to clean, e.g., remove debris and/or moisture, the surgical instrument.

The cleaning device may include an elongated shaft having proximal and distal ends and a cleaning element. The cleaning element is coupled to the distal end of the elongated shaft. The at least one cleaning port is configured and adapted to receive the elongated shaft therein. The at least one cleaning port defines a longitudinal axis, and the cleaning device may be translatable along the longitudinal axis and/or rotatable about the longitudinal axis.

The cleaning element of the cleaning device may be transitionable between compressed and expanded conditions. The cleaning elements may be biased toward the expanded condition. In an embodiment, the cleaning element may define a longitudinal axis and include one or more wings. The wings may be transitionable between a first condition in which the wings are folded toward the longitudinal axis, and a second condition in which the wings are substantially orthogonal to the longitudinal axis. In the second condition, in which the wings are substantially orthogonal to the longitudinal axis, the wings are in greater proximity to the surgical instrument. For example, where the surgical instrument is a viewing instrument, the wings may contact the viewing portion of the viewing instrument.

In an embodiment, a surgical portal apparatus includes a housing member and an inner member. The housing member includes an expandable material that is adapted to transition between a compressed condition and an expanded condition. In the expanded condition, an outer surface of the housing member is adapted for a substantial sealing relationship with tissue upon insertion of the housing member within the tissue for accessing an underlying tissue site. The housing member has leading and trailing ends that define a longitudinal axis. The housing member defines a longitudinal passage for accommodating the inner member therein.

The inner member is operably associated with the housing member and includes one or more longitudinal ports extending therethrough adapted for substantially sealed reception of a surgical object. The inner member further includes a longitudinal cleaning port adapted to store a cleaning device. The cleaning device is configured to remove debris from the surgical object such as an endoscope viewing portion. The cleaning device may rotate about the longitudinal axis of the housing member. In embodiments, the cleaning device may include an elongated shaft having a first end and a second end. The first end is coupled to a handle and the second end is coupled to a cleaning element.

In embodiments, the inner member and the housing member may be disposed in substantially sealed relationship. One or both of the inner member and the housing member may be comprised of an elastomeric material.

These and other embodiments of the present disclosure will be now be described with reference to the accompanying figures.

BRIEF DESCRIPTION OF THE DRAWINGS

Various embodiments of the present disclosure are described hereinbelow with reference to the drawings, wherein.

DETAILED DESCRIPTION OF EMBODIMENTS

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the figures and in the description that follows, like reference numerals identify similar or identical elements. In the following description, well-known functions or constructions are not described in detail to avoid obscuring the present disclosure in unnecessary detail.

A surgical portal apparatus 100 will now be described with reference to FIGS. 1-2B. An example of a housing member is disclosed in commonly assigned U.S. patent application Ser. No. 12/244,024, filed Oct. 2, 2008, the entire contents of which is hereby incorporated herein by reference.

The surgical portal apparatus 100 includes a housing member 102, which includes a plurality of longitudinally extending ports 106a-c and a longitudinally extending cleaning port 130. The surgical portal apparatus 100 is configured and adapted to be placed within an opening "W", e.g., an incision or a naturally occurring bodily orifice (e.g., mouth, anus, or vagina), within tissue "T". To facilitate anchoring of the housing member 102 within opening "W" of tissue "T", the housing member 102 may define a substantially hourglass configuration. In particular, trailing and leading sections 108, 110 may be flanged such that the trailing and leading sections have radial dimensions greater than the radial dimension of opening "W".

The housing member 102 is adapted to establish a substantially sealed relationship within the opening "W" within tissue "T". The housing member 102 may be formed from a compressible and/or flexible material, e.g., a suitable foam or gel, having sufficient compliance to form a seal about one or more surgical instruments 180 (FIGS. 2A and 2B) placed within ports 106a-c, and a cleaning device 135 placed within the cleaning port 130. The compressible and/or flexible material may also be sufficiently compliant to facilitate off-axis movement of surgical instruments 180 placed within respective ports 106a-c. In addition, the compressible and/or flexible material facilitates establishing a substantial seal between the housing member 102 and the opening "W". In particular, the housing member 102 may be compressed to a compressed state during or prior to insertion of the housing member 102 into the opening "W". In the compressed state, the housing member 102 may have a radial dimension less than that of the opening "W". Once placed within the opening "W", the natural biasing force of the material of the housing member 102 will transition the housing member 102 toward the initial, larger radial dimension. This biasing force facilitates the sealed relation between the housing member 102 and the opening "W". Examples of compressible and/or flexible materials suitable for such applications include, but are not limited to, polyisoprene and elastomeric materials.

Figures 1, 2A, 2B:
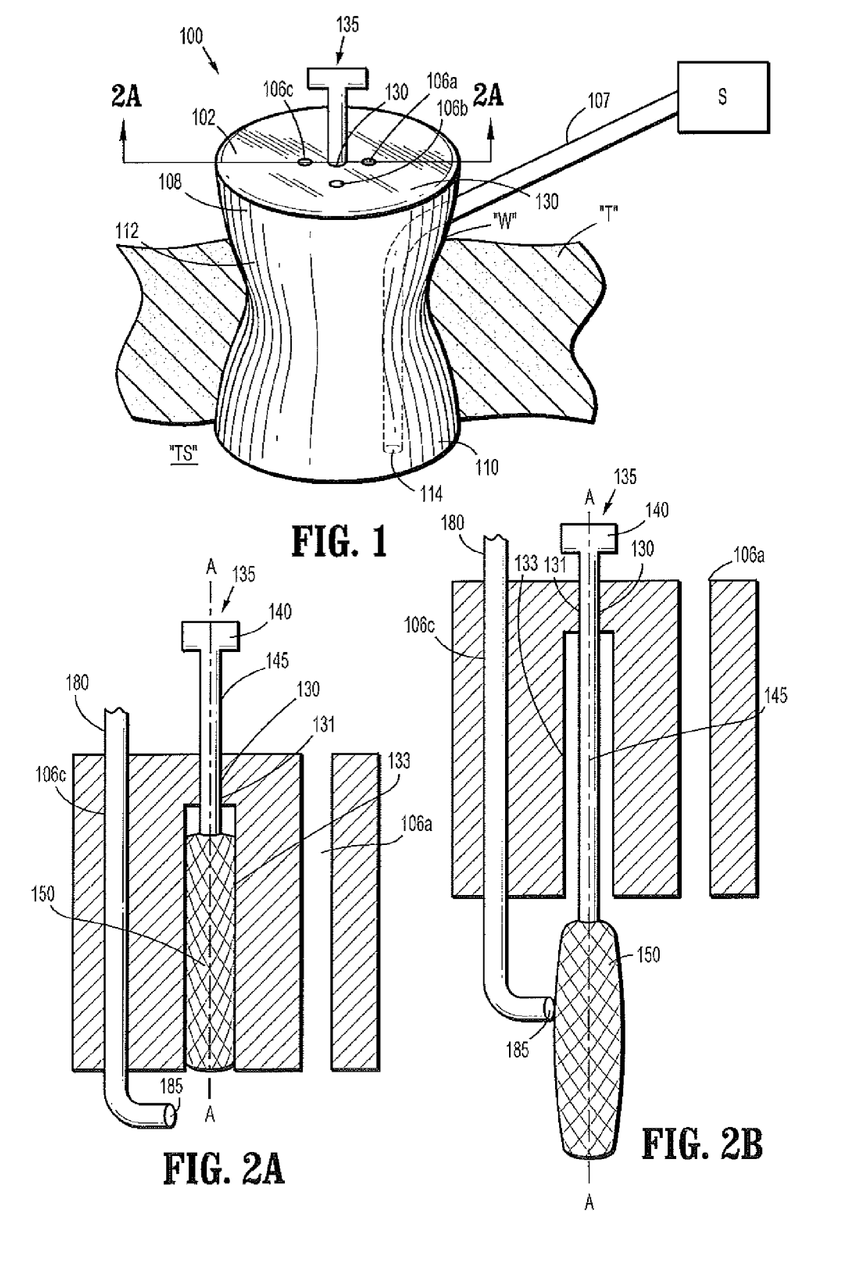
FIG. 1 is a perspective view of a surgical portal apparatus including a cleaning device.
FIG. 2A is a cross-sectional view of the surgical portal apparatus of FIG. 1 including the cleaning device of FIG. 1, taken along section line 2A-2A, shown in a first condition.
FIG. 2B is a cross-sectional view of the surgical portal apparatus of FIG. 1 including the cleaning device of FIG. 1, taken along section line 2A-2A, shown in a second condition.

A method of introducing the surgical portal apparatus 100 within the opening "W" within tissue "T" includes positioning the leading end 110 of housing member 102 within opening "W" and advancing the leading end 110 to a predetermined depth (FIG. 1). Once the housing member 102 is positioned within the opening "W", e.g., with trailing and leading ends 108, 110 of the housing member 102 on opposed sides of the body wall, e.g., the abdominal cavity wall, housing member 102 expands toward its initial, expanded condition in sealed engagement with the tissue defining the opening "W". Surgical instruments 180 are inserted into respective ports 106a-c and the cleaning device 135 is placed within the cleaning port 130.

Once the housing member 102 is placed within the opening "W" of tissue "T", it may be desirable to maintain an enlarged surgical work space. To facilitate maintenance of an enlarged surgical work space, the housing member 102 may also include an insufflation conduit 107 that is operatively coupled to a source of insufflation fluid, e.g., $CO_2$, that communicates insufflation fluid to an underlying tissue site "TS", through an outlet 114, to facilitate maintenance of the enlarged surgical work space.

Each lumen 106a-c of the housing member 102 may be configured and adapted to receive a surgical instrument 180, e.g., a viewing instrument, (FIGS. 2A-2B) in a substantially sealed relationship. Although depicted as including three ports 106a-c configured and adapted to receive surgical instruments 180 therein, the housing member 102 may include a greater or lesser number of lumens that are adapted and configured to receive surgical instruments. Moreover, the ports 106a-e may define a plurality of differently sized diameters. For example, the ports 106a-e may be sized from about 5 mm to about 15 mm. Upon introduction of the surgical instrument 180 through one of the ports 106a-c, the inner surface portions defining the one of the ports 106a-c establishes and maintains a substantial sealed relation about the surgical instrument 180.

A cleaning device 135 (FIG. 3) is configured and adapted to be received within cleaning port 130 of the housing member 102. The cleaning device 135 is configured and adapted to remove debris and/or moisture from the surgical instrument 180, e.g., a viewing instrument. For example, the cleaning device 135 may remove debris and/or moisture from a viewing portion, e.g., a lens, of surgical instrument 180.

Figures 3, 3A:
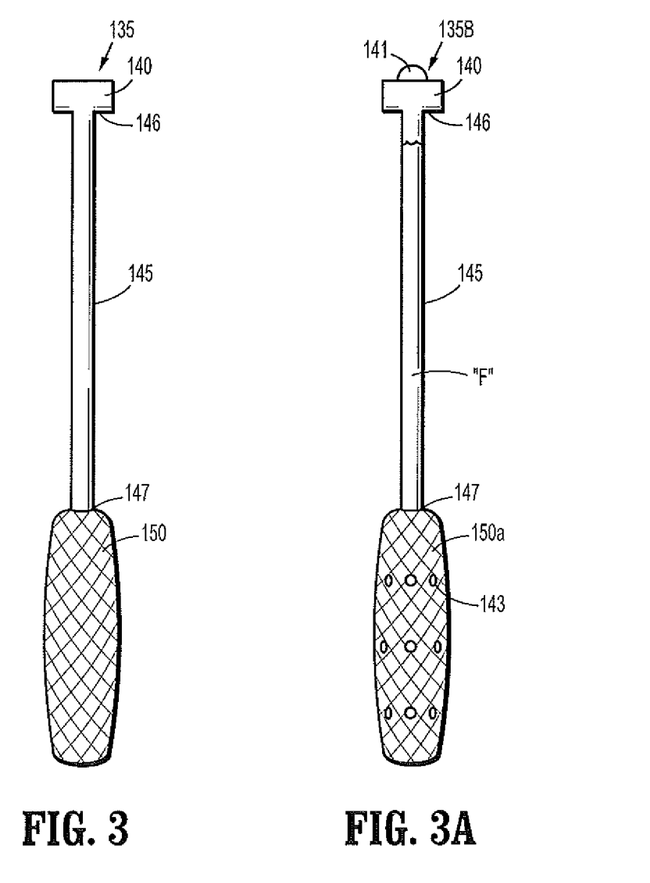
FIG. 3 is a side view of the cleaning device of FIG. 1.
FIG. 3A is a side view of another embodiment of a cleaning device.

As shown in FIG. 3, the cleaning device 135 includes an elongated shaft 145, a handle 140 positioned at a first end 146 of the elongated shaft 145, and a cleaning element 150 positioned at a second end 147 of the elongated shaft 145. The cleaning element 150 may be formed from a biocompatible polymer. In other embodiments, the cleaning element 150 may be formed from an absorbable sponge or an absorbable shape memory polymer. In an embodiment, the cleaning element 150 may be impregnated with a cleaning substance or solution.

In an embodiment, as shown in FIG. 3A, a cleaning device 135B may include elongated shaft 145 including first end 146 and second end 147. The cleaning device 135B may be substituted for the cleaning device 135 of surgical portal apparatus 100. The use and operation of the cleaning device 135E is substantially similar to that of cleaning device 135, except in the following respects that will now be described. The cleaning device 135 includes handle 140 that is coupled to the elongated shaft 145 at the first end 146. In addition, a cleaning element 150a is coupled to the elongated handle 145 at the second end 147. Unlike the cleaning device 135, the cleaning device 135B may include a fluid "F", e.g., a cleaning fluid, that is contained within a reservoir defined within the elongated shaft 145. An actuator 141 operatively coupled to the handle 140 may effect a discharge of the fluid "F" through one or more fluid outlets 143 included in the cleaning element 150a. The actuator 141 may effect the discharge of the fluid "F" through the one or more fluid outlets 143 by increasing the pressure within the reservoir defined by the elongated shaft 145. The fluid "F" may be selectively discharged from the fluid outlets 143 to facilitate cleaning of the surgical instrument 180 positioned in a port 106a-c.

The cleaning element 150, 150a may be a patch or mesh produced from fibers of any biocompatible polymer using any techniques known to those skilled in the art, such as knitting, weaving, tatting, employing non-woven techniques, freeze drying, solvent casting, and the like. It is envisioned that the cleaning element 150 may be formed from any permanent biocompatible materials (e.g., polyesters, polypropylene), biodegradable biocompatible materials (e.g., polylactic acid, polyglycolic acid, oxidized cellulose, and chitosan) or with a combination of both permanent and biodegradable materials, as well as biocompatible polymers listed above.

Examples of polymeric cleaning element 150, 150a may further include nonabsorbable polyester cloth, polyester sheeting, acrylic cloth, polyvinyl sponge or foam, polytetrafluroethylene (PTFE), expanded PTFE, and polyvinyl cloth. In other embodiments, the cleaning element 150 is a mesh, e.g., polypropylene mesh, nylon mesh, and DACRON mesh. Exemplary absorbable meshes include collagen, polyglycolic acid, polyglactin, polycaprolactone, chitosan, and carbon fiber mesh. It should be understood that any of the above-mentioned biocompatible polymers may be suitable for use herein.

The cleaning element 150, 150a may, for example, have an openwork three-dimensional ("3D") structure, e.g., a "honeycomb" structure, and thus a certain thickness separating the two surfaces of the fabric. The shape of the cleaning element 150 may be circular, rectangular, oval-shaped, hook-style, or with any combination thereof. The elongated shaft 145 and handle 140 may be formed, for example, from a polymer selected from a group consisting of nylon, polyvinyl chloride, polytetrafluoroethylene, and combinations thereof.

As shown best in FIGS. 2A and 2B, the cleaning device 135 is positioned within cleaning port 130. The longitudinally extending cleaning port 130 may include a first section 131 defining a first diameter and a second section 133 defining a second diameter. The first diameter 133 may be dimensioned to substantially approximate the diameter of the elongated shaft 145 of the cleaning device 135 to provide stabilization of the elongated shaft 145 and to maintain an insufflated workspace. The elongated shaft 145 is axially translatable through the cleaning port 130 and is rotatable about longitudinal axis A of the cleaning port 130. The cleaning port 130 may also include a second section 133 defining a second diameter 133 dimensioned to substantially approximating the diameter of the cleaning element 150.

As shown in FIGS. 2A and 2B, the surgical instrument 180 includes a viewing portion 185. The surgical instrument 180 may be positioned within any of the ports 106a-c. As shown in FIGS. 2A and 2B, the surgical instrument 180 is positioned within port 106c. The use and operation of the cleaning device 135 to facilitate removal of debris and/or moisture from the viewing portion 185 of the surgical instrument 180 positioned within one of the ports 106a-c will now be described.

As shown in FIG. 2A, the cleaning device 135 is positioned within cleaning port 130 such that the cleaning element 150 is fully or substantially retracted within the second section 133 of the cleaning port 130. The distal advancement of the cleaning device 135 through cleaning port 130 distally slides the cleaning element 150 through the second section 133. The cleaning element 150 may be transitionable between a compressed diameter and an expanded diameter, and may be biased toward the expanded diameter. Accordingly, upon distal translation through and out from the cleaning port 130, the cleaning element 150 may transition toward the expanded diameter, thereby coming into contact with instrument 180 positioned within one of ports 106a-c.

Furthermore, the instrument 180 may be rotated or positioned such that the viewing portion 185 of the instrument 180 comes into contact with the cleaning element 180. Once contact between the viewing portion 185 and the cleaning element 150 has been made, the cleaning device 135 may be rotated to effect sliding of the cleaning element 150 across the viewing portion 185. The cleaning device 135 may also be alternatively proximally withdrawn and distally translated within the cleaning port 130 to effect sliding of the cleaning element 150 across the viewing portion 185. The frictional contact between the cleaning element 150 and the viewing portion 185 facilitates cleaning, e.g., removal of debris and/or moisture, of the viewing portion 185 of the instrument 180. Once the instrument 180, and in particular viewing portion 185, has been cleaned, the cleaning device 135 may be retracted by proximally translating the cleaning device 135 through the cleaning port 130.

Figure 4:
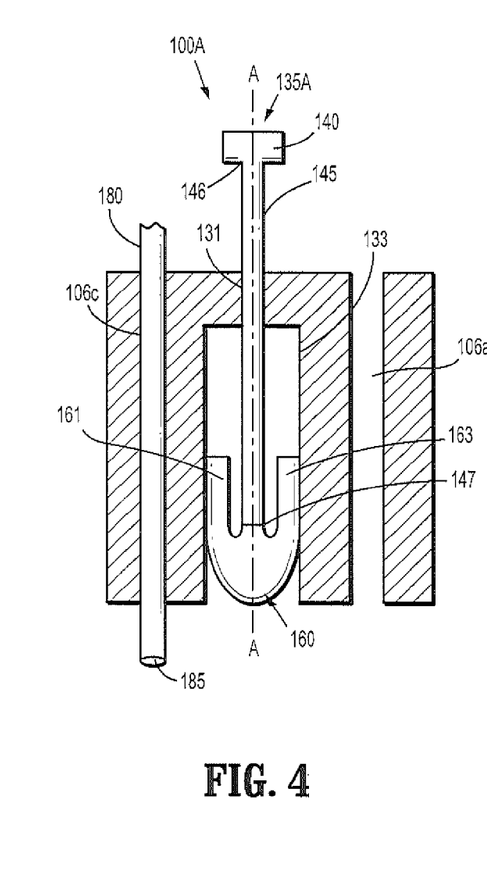
FIG. 4 is a cross-sectional view of another embodiment of a surgical portal apparatus including another embodiment of a cleaning device inserted therein and shown in a first retracted condition.
Figure 5:
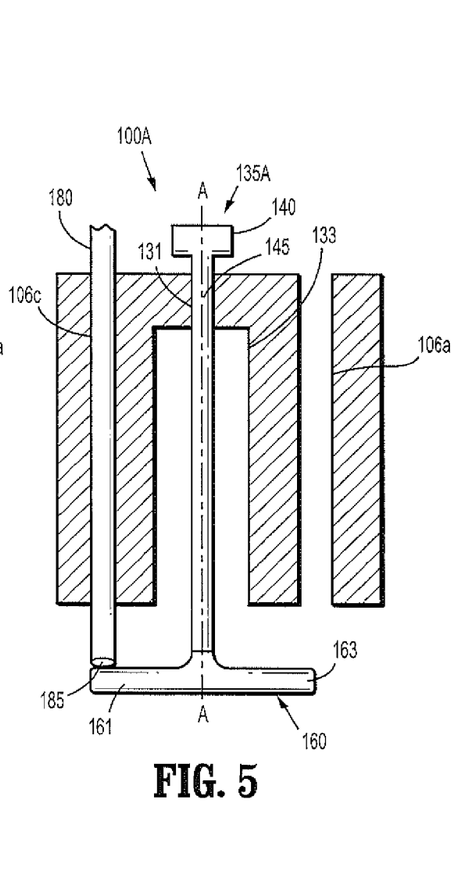
FIG. 5 is a cross-sectional view of the surgical portal apparatus of FIG. 4 including the cleaning device of FIG. 4 shown in a deployed condition.
Figure 6:
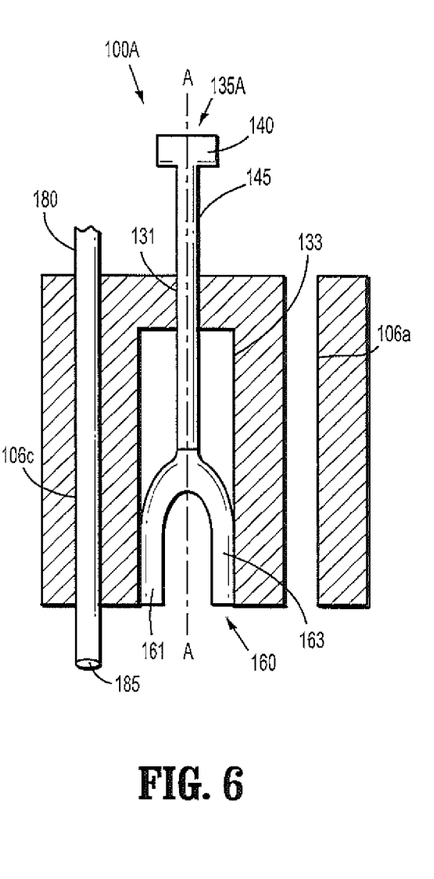
FIG. 6 is a cross-sectional view of the surgical portal apparatus of FIG. 4 including the cleaning device of FIG. 4 shown in a second retracted condition.

Another embodiment of a surgical portal apparatus will now be described with reference to FIGS. 4-6. The surgical portal apparatus 100A, shown in FIGS. 4-6, is substantially similar to the surgical portal apparatus 100 except in the following ways, which will now be described. In particular, the surgical portal apparatus 100A includes a cleaning device 135A that is substantially similar to the cleaning device 135, except in the following respects which will now be described.

In particular, the cleaning device 135A may include a cleaning element 160 disposed at the distal end 147 of the elongated shaft 145. The cleaning element 160 includes one or more deployable wings 161, 163. The one or more wings 161, 163 of the cleaning element 160 are biased toward a deployed condition, as shown in FIG. 5. In the deployed condition, the wings 161, 163 are substantially orthogonal to longitudinal axis A and are positioned distal to the distal end of at least one port 106a-c. With the wings 161, 163 deployed, as shown in FIG. 5, the wings 161, 163 are positioned to contact the viewing portion 185 of the instrument 180. Although shown as including two wings 161, 163, the cleaning device 135A may include a greater or lesser number of wings. The cleaning device 135A may be rotated about longitudinal axis A to bring the cleaning element 160 into contact with the viewing portion 185 of instrument 180, and to effect a sliding engagement between the wings 161, 163 and the viewing portion 185 to thereby facilitate removal of debris and/or moisture from the viewing portion 185.

As shown in FIGS. 4 and 6, when the cleaning device 135A is retracted within the second section 133 of the cleaning port 130, the wings 161, 163 are folded and compressed within the second section 133. In particular, as shown in FIG. 4, the wings 161, 163 may be folded in a proximal direction. Alternatively, as shown in FIG. 6, the wings 161, 163 may be folded in a distal direction. In particular, prior to deployment of the wings 161, 163, the wings 161, 163 may be folded in the proximal direction (FIG. 4) to facilitate initial deployment of the wings 161, 163. Subsequent to the initial deployment, the wings 161, 163 may fold distally (FIG. 6). Thereafter, the cleaning device 135A may be repeatedly deployed (FIG. 5) and retracted as shown in FIG. 6, as desired.

Moreover, the wings 161, 163 of the cleaning element 160 may be bent at an angle between about zero degrees (0°) to about ninety degrees (90°) to make it easier to clean surgical object's components, such as viewing portion 185 of instrument 180. In an embodiment, the cleaning element and/or its wings 161, 163 may be formed from a shape memory polymer, e.g., a material that is capable of being temporarily deformed by mechanical force and then caused to revert back to an original shape when stimulated by energy.

Figure 7:
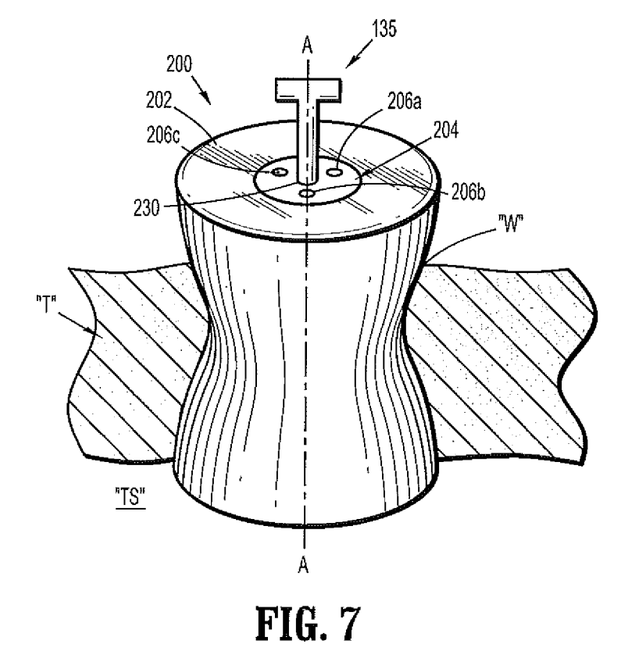
FIG. 7 is a perspective view of a surgical portal apparatus having a housing member and an inner member in accordance with an embodiment of the present disclosure.

Another embodiment of a surgical portal apparatus will now be described with reference to FIGS. 7-9. The surgical portal apparatus 200, illustrated in FIGS. 7-9, is substantially similar to the surgical portal apparatus 100 described above, except in the following respects which will now be described.

The surgical portal apparatus 200 includes a housing member 202 and an inner member 204. The inner member 204 includes a cleaning port 230 that is substantially similar to cleaning port 130 described above and is configured and adapted to receive a cleaning device 135, 135A therethrough. In addition, the inner member includes one or more longitudinally extending ports 206a-c that are adapted and configured to receive instruments therethrough, e.g., instrument 180. The ports 206a-c may form a substantial seal about the instruments inserted within the ports 206a-c.

Figure 8:
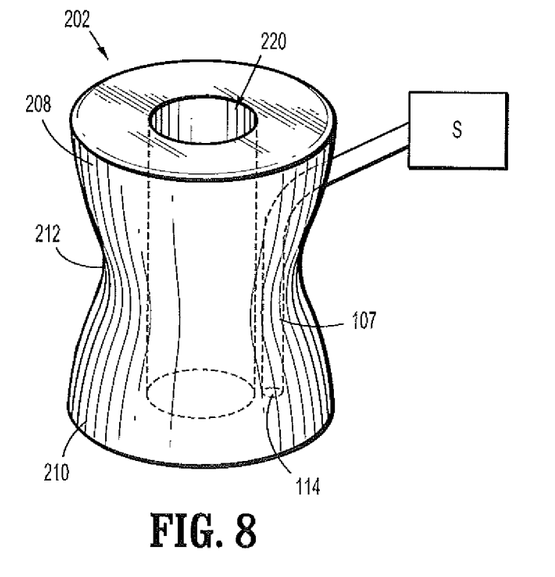
FIG. 8 is a perspective view of the housing member of the surgical portal apparatus of FIG. 4 with the inner member removed.
Figure 9:
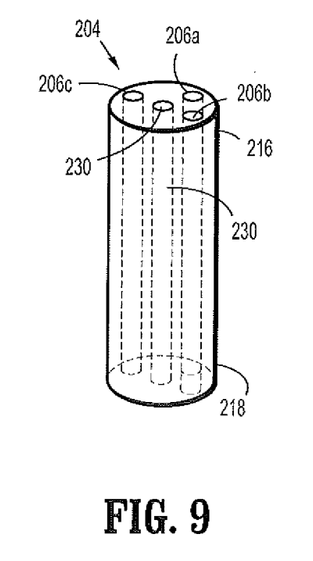
FIG. 9 is a perspective view of the inner member of the surgical portal apparatus of FIG. 1 in accordance with the present disclosure.

As shown in FIGS. 8-9, the housing member 202 includes trailing and leading ends 208, 210, respectively, and an intermediate section 212 disposed therebetween. Additionally, as described above with respect to surgical portal apparatus 100, the housing member 202 may also include insufflation conduit 107, which is operatively coupled to source S of insufflation fluid, e.g., $CO_2$, that provides and maintains a flow of insufflation fluid through outlet 114 into the underlying tissue site "TS" (FIG. 7).

The housing member 202 (FIG. 8) may define an hourglass configuration, as shown, to facilitate anchoring of the housing member within opening "W" within tissue "T". The housing member 202 includes a longitudinally extending passage 220 adapted and configured for the reception of the inner member 204 (FIG. 9) therein. Upon insertion of the inner member 204 within the passage 220, the inner member 204 compresses to fit within the passage 220 in a substantially sealed relation. When inner member 204 is located within the longitudinal passage 120 of housing member 102, e.g., with leading and trailing ends 218, 216 of the inner member 204 on opposed sides of the body wall (e.g., the abdominal cavity wall), inner member 204 expands toward its normal expanded condition (which it naturally biases towards regardless of its position relative to the longitudinal passage 220) in sealed engagement with the inner boundary of longitudinal passage 220 of housing member 202. In an embodiment, the inner member 204 may be rotated relative to longitudinal axis A of the housing member 202 when the inner member 204 is positioned within the housing member 202 (FIG. 7).

Although the cleaning element 150, 150a, 160 is described as cleaning the viewing portion 185 of instrument 180, it should be understood that the cleaning element 150 may clean other surgical instruments or parts of surgical instruments, e.g., a light source (not shown).

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical portal apparatus, comprising: a cleaning device including an elongated shaft and a cleaning element having a first end and a second end, wherein the elongated shaft is coupled to the cleaning element at a distal end of the elongated shaft between the first end and the second end of the cleaning element such that the elongated shaft and the cleaning element form a T-shape; and a housing member including: a leading portion; a trailing portion; and an intermediate portion disposed between the leading and trailing portions; one or more instrument ports longitudinally extending between the leading and trailing portions, the one or more instrument ports configured and adapted to receive a surgical instrument therein; and at least one cleaning port extending between the leading and trailing portions, the at least one cleaning port configured and adapted to receive the cleaning device therein, the cleaning device configured and adapted to clean the surgical instrument; wherein the cleaning element is transitionable between a folded condition and an expanded condition, wherein the first end and the second end diametrically oppose each other in the folded condition, and wherein a portion of the cleaning element extends to at least one of the one or more instrument ports in the expanded condition.

2. The surgical portal apparatus of claim 1, wherein the at least one cleaning port defines a longitudinal axis, the cleaning device translatable along the longitudinal axis.

3. The surgical portal apparatus of claim 1, wherein the at least one cleaning port defines a longitudinal axis, the cleaning device rotatable about the longitudinal axis.

4. The surgical portal apparatus of claim 1, wherein the cleaning element is biased toward the expanded condition.

5. The surgical portal apparatus according to claim 1, wherein the cleaning element is formed from an absorbable material.

6. The surgical portal apparatus according to claim 1, wherein the cleaning element is formed from a biocompatible material.

7. The surgical portal apparatus according to claim 1, wherein the at least one cleaning port includes a first portion configured and dimensioned to receive the elongated shaft of the cleaning device in a sealing relation therewith.

8. The surgical portal apparatus according to claim 7, wherein the at least one cleaning port further includes a second portion configured and dimensioned to receive the cleaning element in the folded condition.

9. The surgical portal apparatus according to claim 8, wherein the first and second ends of the cleaning element are configured to be flush with a distal end of the at least one cleaning port when the cleaning element is in the folded condition.

10. A surgical portal apparatus, comprising:
- a housing member comprising an expandable material being adapted to transition between a compressed condition and an expanded condition in which an outer surface of the housing member is adapted for a sealing relationship with tissue upon insertion of the housing member into the tissue for accessing an underlying tissue site, the housing member defining a longitudinal axis and having leading and trailing ends;
- a cleaning device including an elongated shaft and a cleaning element, wherein the cleaning element is coupled to a distal end of the elongated shaft between a first end and a second end of the cleaning element such that the elongated shaft and the cleaning element form a T-shape, the cleaning element being transitionable between a proximal folded condition, an expanded condition and a distal folded condition; and
- an inner member operably associated with the housing member and including:
  - at least one longitudinal access port extending therethrough, the at least one longitudinal access port adapted for sealed reception of a surgical object; and
  - a longitudinal cleaning port adapted to store the cleaning device, the cleaning device configured to remove debris from the surgical object, and wherein the cleaning element extends to the at least one longitudinal access port in the expanded condition.

11. The surgical port apparatus according to claim 10, wherein the longitudinal cleaning port has a first diameter and a second diameter, the first diameter is smaller than the second diameter.

12. The surgical portal apparatus according to claim 10, wherein the inner member is rotatable about the longitudinal axis.

13. The surgical portal apparatus according to claim 10, wherein the inner member is separable from the housing member.

14. The surgical portal apparatus according to claim 10, wherein at least one of the inner member and the housing member is comprised of an elastomeric material.

15. The surgical portal apparatus according to claim 10, wherein the cleaning element is oriented adjacent to the elongated shaft in the proximal folded condition, and wherein the cleaning element is oriented 180 degrees from the elongated shaft in the distal folded condition.

16. The surgical portal apparatus according to claim 10, wherein an end of the cleaning element is spaced apart from the elongated shaft in the distal folded condition.

\* \* \* \* \*